United States Patent [19]

Reid

[11] Patent Number: 4,970,893
[45] Date of Patent: Nov. 20, 1990

[54] TILT ANGLE TESTER

[76] Inventor: Philip L. Reid, 400 S. Danzler Rd., Duncan, S.C. 29334

[21] Appl. No.: 485,602

[22] Filed: Feb. 27, 1990

[51] Int. Cl.⁵ .......................................... G01N 13/02
[52] U.S. Cl. .................................................... 73/64.4
[58] Field of Search ............................ 73/64.4, 64, 54

[56] References Cited

U.S. PATENT DOCUMENTS 2,054,438  9/1936  Natelson ............................... 73/64.4

FOREIGN PATENT DOCUMENTS 147414  4/1981  German Democratic Rep. ..................................... 73/64.4
167239  7/1988  Japan ..................................... 73/64.4

Primary Examiner—Hezron E Williams
Assistant Examiner—Joseph W. Roskos
Attorney, Agent, or Firm—Bailey & Hardaway

[57] ABSTRACT

An apparatus for measuring the surface of a substrate has a normally horizontal surface for mounting a solid thereon, a device for rotating the surface and a counter synchronized with the rotational device to indicate the amount of rotation and a switch for simultaneously initiating activation of the rotating device and synchronized counter and for simultaneously deactivating both the rotational device and the synchronized counter.

5 Claims, 2 Drawing Sheets

4,970,893

TILT ANGLE TESTER

BACKGROUND OF THE INVENTION

This invention relates generally to the art of printing and more particularly to the art of measuring the printability of a substrate.

In the art of printing, it has been known that the ability of a substrate surface to receive and retain print media is related to the surface tension of that substrate. This degree of surface tension can be measured in relative terms by the placement of a drop of liquid upon that surface while in the horizontal state. The surface with the drop of liquid thereon is then rotated until the drop of liquid begins to run. The angle of rotation is proportional to the surface tension of the substrate surface and thus indicative of the ability of that surface to receive and retain a printing medium. A substrate with a high surface tension receives and retains a printing medium better than a substrate with a lower surface tension.

Various prior art attempts have been made to quantify surface tension. Such efforts have normally involved the use of an electric motor to tilt a horizontal surface with an operator having the ability to deactivate the supply of electricity to the electric motor when a drop of liquid runs on the horizontal surface. After deactivating the electric motor, the angle of the surface is then measured.

The prior art process has suffered from the disadvantages of lack of reproduceability and a lack of standardization.

SUMMARY OF THE INVENTION

It is thus an object of this invention to provide a novel apparatus and process for measuring the surface tension of a solid substrate.

It is a further more particular object of this invention to provide a novel apparatus and process for measuring the surface tension of a substrate which lends itself to standardization and reproduceability.

These as well as other objects are accomplished by an apparatus having a normally horizontal surface for mounting a solid thereon, means for rotating the surface and means synchronized with the rotational means to indicate the amount of rotation and means for simultaneously initiating activation of the rotating means and synchronized means and for simultaneously deactivating both the rotational means and the synchronized means.

DETAILED DESCRIPTION

In accordance with this invention, it has been discovered that the difficulty associated with prior art processes had been related to the inherent properties of the electric motors utilized for rotating horizontal surfaces upon which a liquid drop is placed. The difficulty brought about by this inherent problem is that electric motors have a built-in momentum which causes rotation to continue even after removing the source of electricity. This momentum varies from motor to motor such that when measuring an angle of rotation if operators respond exactly in the same fashion, the measured angle will be different each time. Thus in accordance with this invention, it has been found that if means are provided which are synchronized with the degree of rotation which will stop immediately upon deactivation, that the measurement of the synchronized means provides a precise measurement of the angle observed by the operator when the running of a drop of liquid occurs.

The synchronized means in accordance with this invention preferably take the form of a pulse generator associated with the electric motor which provides a pulse indicative of the degree of rotation provided and a counter to count the pulses which is frozen upon the operator indication that a drop of liquid has begun to run. The counter immediately freezes the reading even though the electric motor may continue to rotate. Various other advantages and features will become apparent from a reading of the following description given with reference to the various figures of drawings.

Figure 1:
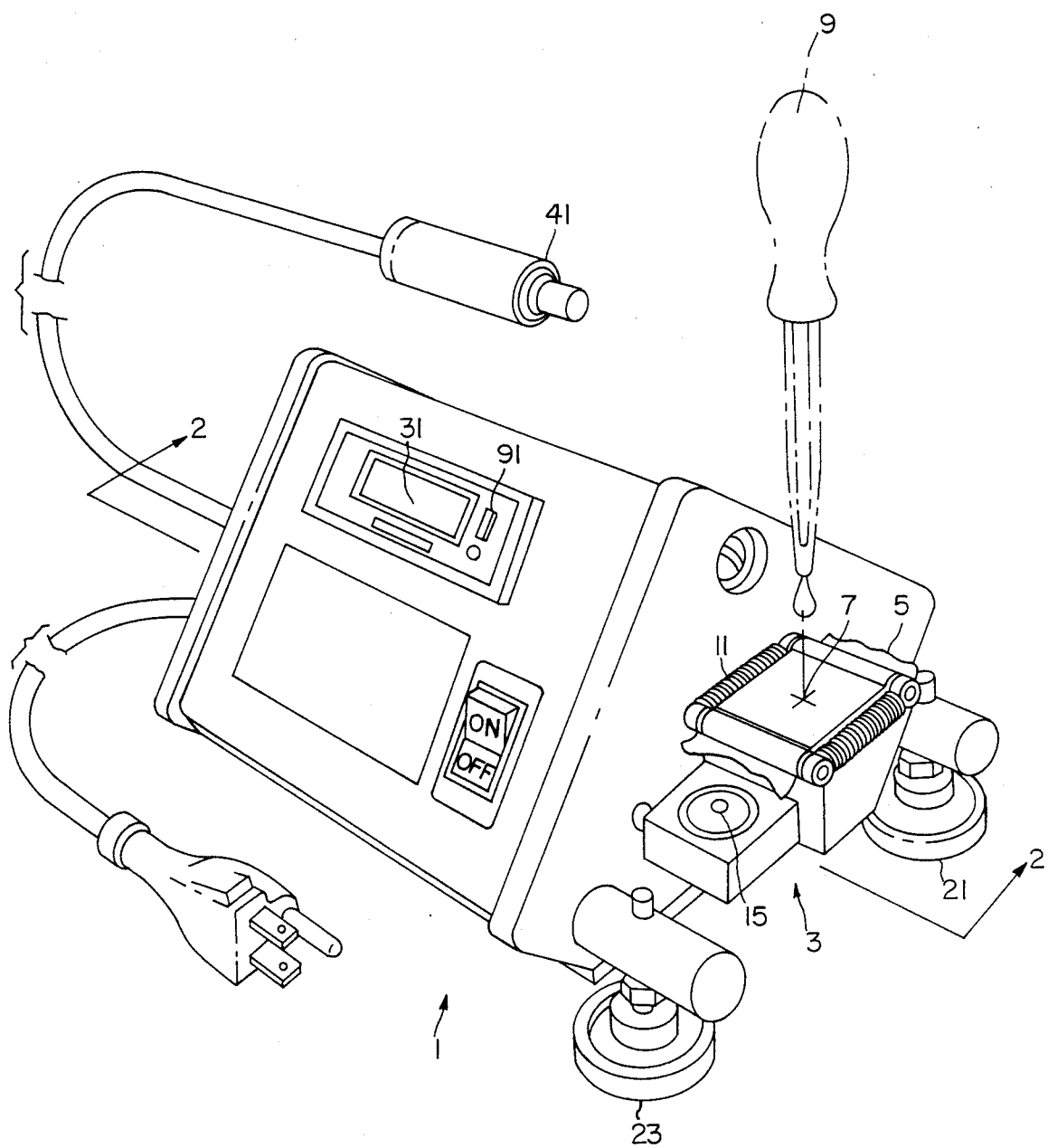
FIG. 1 of the drawings is a prospective view of the apparatus in accordance with this invention.

FIG. 1 of the drawings illustrates the apparatus 1 in accordance with this invention. The apparatus is provided with a stage 3 for the placement of a substrate such as a piece of packaging film 5 thereon. The stage receives a drop of liquid at the mid portion 7 thereof by means such as dropper 9. Stage 3 is provided with means such as spring-loaded tighteners 11 to maintain film 5 in a taut state. Stage 3 is provided with a bubble level 15 in order to assure horizontal orientation prior to any testing. The apparatus 1 is provided with adjustable legs 21 and 23 to assure proper orientation. The apparatus 1 has a display 31 which is indicative of the degree of rotation of stage 3. Display 31 is associated with synchronized means to be further described below and displays a measurement indicative of the amount of rotation of stage 3. Means 41 are provided to initiate rotation of the stage 3 and simultaneously initiate a reading on the display 31 indicative of the amount of rotation. Means 41 upon deactivation deactivates and freezes the display 31. The numeral reading on display 31 is thus an indication of the angle of the stage 3 at the point in time when the observer detects the drop of liquid beginning to run. Preferably means 41 also deactivates the electric motor which is rotating the stage 3.

Figure 2:
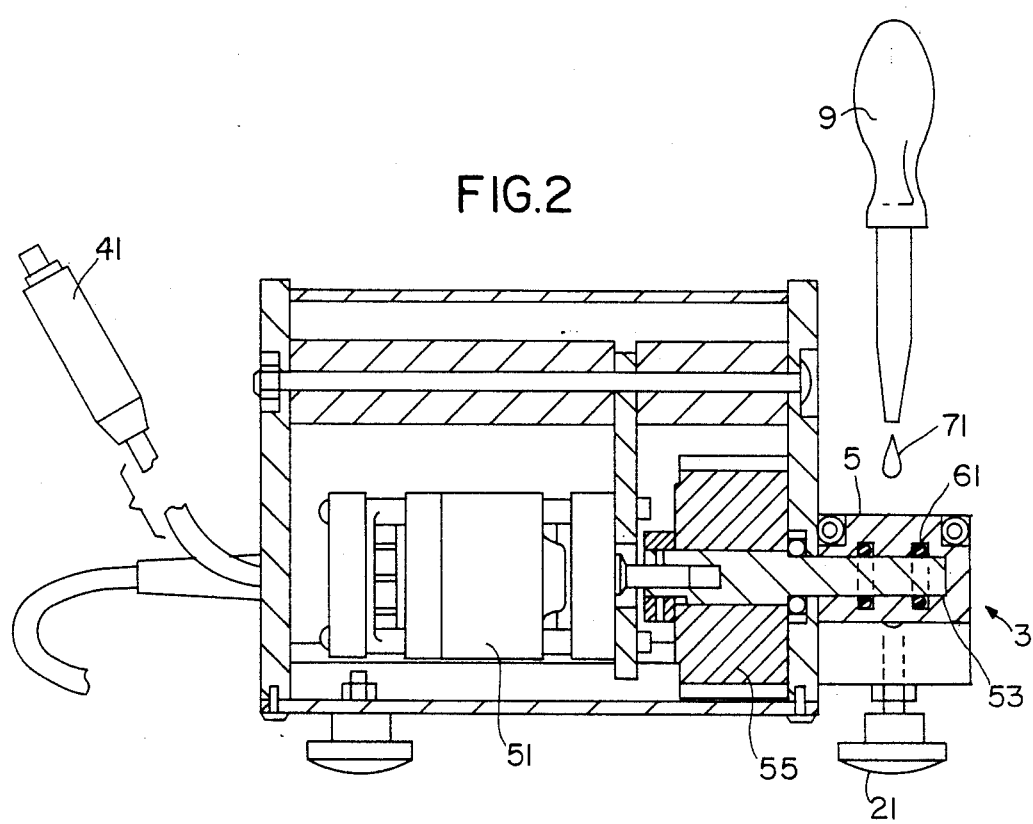
FIG. 2 of the drawings is a cross-sectional view along the line 2—2 of FIG. 1.
Figure 3:
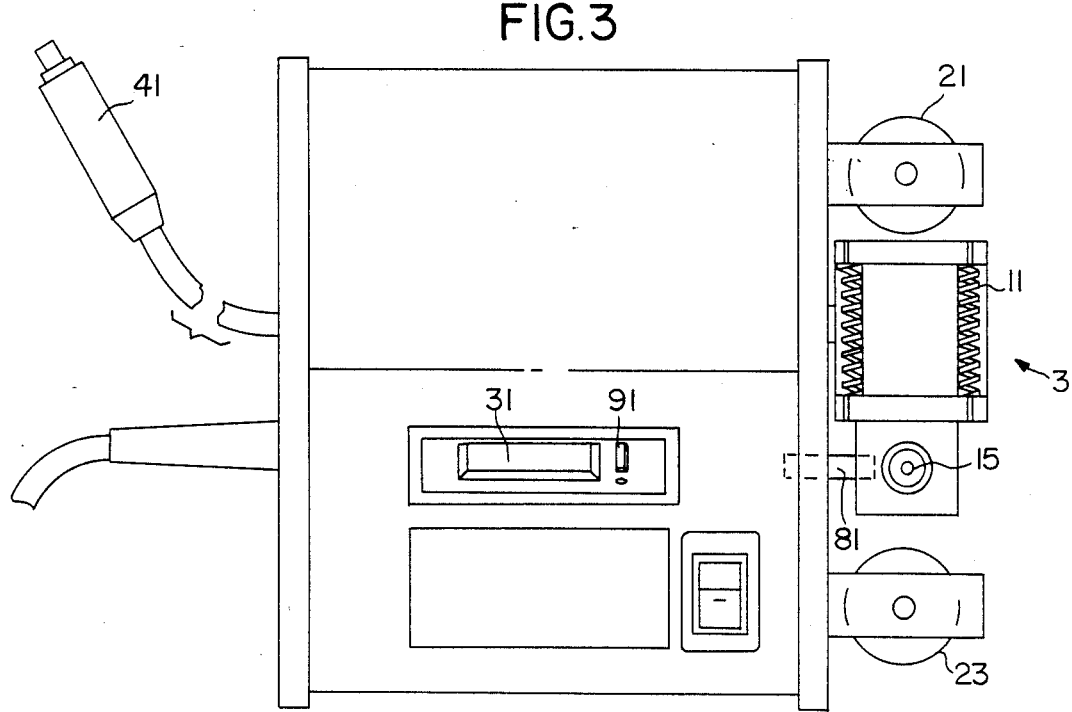
FIG. 3 of the drawings is a top view of the apparatus of FIG. 1.

Referring to FIG. 2 of the drawings which is a cross-sectional view along the line 2—2 of FIG. 1, it is seen that an electric motor 51 operates through a shaft 53 to rotate stage 3. Shaft 53 has associated therewith synchronized means indicative of the degree of rotation of the shaft 53 and thus stage 3. Synchronized means illustrated here comprise a pulse generator 55, associated with a counter and display 31.

Means 41 is a switch which simultaneously initiates a supply of electricity to motor 51 and initiates as well synchronized means such as pulse generator 55 and the counting thereof on display 31. Means 41 also upon deactivation immediately freezes the count on display 31 while disrupting the supply of electricity to motor 51. The display 31 thus has the numeral indicative of the degree of rotation at the instant of observation by the operator even though motor 51 may continue to rotate.

It is understood that the synchronized means in accordance with this invention may be means other than a pulse generator and a counter which is the preferred embodiment. Such other synchronized means may be in the form of a timer which freezes a display upon an deactivation by an operator. In accordance with this invention the following are given as preferred features of the invention. The motor 51 preferably operates at rotational speed of 1 rpm so as to rotate the stage 3 in the counter-clockwise direction when observed from the left of FIG. 1. Pulse generator preferably has 3600 pulses per 360 degrees such that each pulse is indicative of 0.1 degrees. Electric motor 51 is preferable Granger No. 4Z451, 1 R.P.M. gearhead motor 0.001 of a horsepower. A preferred pulse generator is manufactured by Hohner and a preferred counter is Veeder-Root No. 799625-027 count.

In operation stage 3 is initially leveled by appropriately adjusting adjustable legs 21 and 23 as well as by rotating stage 3 with respect to shaft 53. From the FIG. 2 cross section, it can be seen that stage 3 is frictionally mounted upon shaft 55 by o-rings 61 to permit manual rotation of the stage 3 with respect to the shaft 53 until it contacts stop pin 81. A drop of a liquid such as water 71 is then placed upon the stage means 3 and switch 41 actuated by the operator while the operator observes the drop of water 71 upon the stage 3 having a solid substrate 5 thereon. Upon the running of the drop 71 the operator deactivates the means 41 thus freezing the display on counter 31. If the counter 31 displayed 10.7 counts, for example, that would be indicative of 10.7 degrees of tilt from the horizontal. The ten and one tenth four degrees may be directly correlated to the surface tension of the substrate. A push button switch 91 is provided to allow the counter to be reset to a zero count at same time a stage 3 is releveled, prior to the next test.

It is thus seen that the process and apparatus of this invention provides a novel apparatus and process for the measurement of the surface tension of a solid substrate. It is further seen that the process and apparatus of this invention provide a process and apparatus which provides reproducible, consistent measurements of such surface tension. As various modifications will become apparent to those skilled in the art from a reading of the foregoing description which is exemplary in nature such modifications are embodied with the spirit and scope of this invention as defined by the following appended claims.

That which is claimed is:

1. An apparatus for testing the surface tension of a solid, comprising:
    a normally horizontal stage surface for mounting said solid thereon;
    means for rotating said surface so as to tilt same with regard to horizontal;
    means for placing a drop of liquid upon said solid while in the horizontal position;
    means synchronized with said means for rotating to indicate the amount of rotation thereof;
    means for simultaneously initiating activation of said means for rotating and said synchronized and for simultaneously deactivating said means for rotating and said synchronized means.

2. The apparatus according to claim wherein said synchronized means is a pulse generator and a counter for counting the pulse of said pulse generator.

3. The apparatus according to claim 1 including a bubble level associated with said horizontal surface to indicate the horizontal orientation thereof.

4. The apparatus according to claim 1 wherein said means for rotating comprises a rotary motor and a horizontal shaft and said horizontal surface is mounted on said horizontal shaft with O-rings located between said horizontal surface and said shaft to permit said horizontal surface to be manually rotated with respect to said shaft.

5. A process for measuring the surface tension of a solid comprising;
    placing a drop of liquid upon said solid while in a horizontal state;
    simultaneously initiating rotation of said horizontal surface and synchronized means indicative of the amount of rotation of said surface;
    observing said drop of liquid;
    deactivating said synchronized when said liquid runs on said solid.

* * * * *